United States Patent
Saur et al.

(10) Patent No.: US 10,989,911 B2
(45) Date of Patent: Apr. 27, 2021

(54) METHOD FOR OPERATING A MEDICAL-OPTICAL DISPLAY SYSTEM

(71) Applicant: Carl Zeiss Meditec AG, Jena (DE)

(72) Inventors: Stefan Saur, Aalen (DE); Christopher Käsbach, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 512 days.

(21) Appl. No.: 15/951,909

(22) Filed: Apr. 12, 2018

(65) Prior Publication Data

US 2018/0307034 A1     Oct. 25, 2018

(30) Foreign Application Priority Data

Apr. 20, 2017 (DE) ................. 10 2017 108 371.5

(51) Int. Cl.
  *G06T 11/60* (2006.01)
  *G02B 23/10* (2006.01)
  (Continued)

(52) U.S. Cl.
  CPC ............ *G02B 23/10* (2013.01); *A61B 1/0005* (2013.01); *A61B 1/00009* (2013.01); *A61B 1/04* (2013.01);
  (Continued)

(58) Field of Classification Search
  CPC ... A61B 1/04; A61B 1/0005; A61B 2090/365; A61B 2090/366; A61B 90/20; A61B 1/00009; A61B 2090/368; G02B 21/0012; G02B 21/361; G02B 21/365; G02B 21/367; G06T 2207/10056; G06T 19/006; G06T 7/0012–0016; G06T 2207/30004–30104; G06K 9/00671
  See application file for complete search history.

(56) References Cited

U.S. PATENT DOCUMENTS

2004/0070822 A1   4/2004  Shioda et al.
2011/0321084 A1  12/2011  Takahashi et al.
(Continued)

FOREIGN PATENT DOCUMENTS

DE   10 2014 210 150    12/2015
JP         09-56669      3/1997
(Continued)

OTHER PUBLICATIONS

German Office Action for 10 2017 108 371.5 dated Sep. 29, 2017.
Notice of the Reason for Refusal for Application No. 2018-073624 (5 pages).

*Primary Examiner* — Brian Werner
(74) *Attorney, Agent, or Firm* — Nixon Peabody LLP; Jeffrey L. Costellia

(57) ABSTRACT

A method for operating a medical-optical display system for displaying an object image of an observed object is made available, said object image having been obtained by means of a medical-optical observation apparatus wherein the medical-optical display system comprises a data superimposition unit for superimposing data of at least one image data record into the object image. The method comprises the following steps: determining at least one region with little activity within the object image and superimposing the at least one image data record into the at least one region with little activity.

14 Claims, 5 Drawing Sheets

(51) Int. Cl.
*A61B 1/04* (2006.01)
*A61B 1/00* (2006.01)
*G06T 7/00* (2017.01)
*G02B 21/00* (2006.01)
*G02B 21/20* (2006.01)
*G02B 21/36* (2006.01)
*G06T 7/254* (2017.01)
*A61B 90/00* (2016.01)
*A61B 34/20* (2016.01)
*A61B 90/30* (2016.01)
*A61B 90/20* (2016.01)

(52) U.S. Cl.
CPC ......... *G02B 21/0012* (2013.01); *G02B 21/20* (2013.01); *G02B 21/364* (2013.01); *G02B 21/365* (2013.01); *G06T 7/0012* (2013.01); *G06T 7/254* (2017.01); *G06T 11/60* (2013.01); *A61B 90/20* (2016.02); *A61B 90/30* (2016.02); *A61B 90/361* (2016.02); *A61B 2034/2055* (2016.02); *A61B 2090/3784* (2016.02); *G06T 2207/10021* (2013.01); *G06T 2207/10056* (2013.01)

(56) References Cited

U.S. PATENT DOCUMENTS

| | | | |
|---|---|---|---|
| 2016/0183779 A1* | 6/2016 | Ren | A61B 3/132 351/206 |
| 2016/0232682 A1 | 8/2016 | Nakagawa et al. | |
| 2017/0035287 A1* | 2/2017 | Ren | A61B 3/13 |

FOREIGN PATENT DOCUMENTS

| | | |
|---|---|---|
| JP | 2012-10117 | 1/2012 |
| JP | 2014-042660 | 3/2014 |
| WO | WO-2015-041177 A1 | 3/2015 |

* cited by examiner

METHOD FOR OPERATING A MEDICAL-OPTICAL DISPLAY SYSTEM

The present application claims priority to German Application No. 10 2017 108 371.5 filed Apr. 20, 2017, the disclosure of which is hereby incorporated by reference herein in its entirety.

BACKGROUND OF THE INVENTION

Field of the Invention

The invention relates to a method for operating a medical-optical display system having a data superimposition apparatus. Further, the invention relates to a computer program product for carrying out such a method and to a medical-optical display system having a data superimposition apparatus.

Description of Related Art

A medical-optical observation apparatus in which an image data record with additional information items is mirrored into an image provided by the medical-optical observation apparatus by means of a device for mirroring-in data is known from DE 10 2014 210 150 A1.

In general, the position in the image into which the image data record is mirrored is set by the device for superimposing data, without reference being made in the process to the image content of the image.

In an inexpedient case, the superposition is effectuated exactly at the position at which the user (e.g. a surgeon or a theatre nurse) would like to have an "unimpeded view" of the real scene (site, displays, appliances, persons, . . . ).

In some information items to be augmented, a spatially accurate superposition is desired (e.g. tumour contour data), but the positioning is not bound to a fixed position in the case of many information items (e.g. status reports of an appliance); i.e., ideally, the information items of the image data record would be superimposed where they do not impede as there is no action/activity in this region at the current time.

There are approaches in which a superposition of an image data record is effectuated relative to surgical instruments (e.g. a tip of a tool). However, these approaches are disadvantageous in that there has to explicitly be tool recognition (in the extreme case, the algorithm must be newly parametrized for each new tool set).

Further, in the case of data superimposition, it is known to carry out fixed coding of the position for superposition in pixel coordinates without taking account of image contents, to take account of the geometry of a space such that the data superimposition is always effectuated in front of the object, and to dock the data superimposition to a surgical instrument, for example.

With reference to the aforementioned prior art, it is an object of the present invention to make available an advantageous method for operating a medical-optical observation apparatus, in particular an operating microscope, and a medical-optical observation apparatus, in which there is no masking of relevant image contents in the case of a data superimposition of an image data record.

The aforementioned object is achieved by a method according to claim 1 and by a medical-optical observation apparatus according to claim 9. The dependent claims contain advantageous embodiments of the invention.

SUMMARY OF THE INVENTION

According to the invention, a method for operating a medical-optical display system for displaying an object image of an observed object is made available, said object image having been obtained by means of a medical-optical observation apparatus, wherein the medical-optical display system comprises a data superimposition unit for superimposing data of at least one image data record into the object image. The method comprises the following steps:
  determining at least one region with little activity within the object image and
  superimposing the at least one image data record into the at least one region with little activity.

Consequently, the invention chooses a novel approach for avoiding unwanted masking of image contents, which would be accompanied by a loss of information.

Here, the object image may also be a stereo image which is constructed from a right and left partial image. Then, the image data record can be superimposed either into the left partial image or into the right partial image. However, it is also possible to superimpose the image data record into both the right partial image and the left partial image. In particular, the image data record may then comprise a right and a left image data record which, together, yield a stereoscopic image data record. Then, the image information item superimposed by means of the image data record can be a stereoscopic image information item. However, the object image can also be an image of the surroundings displaying the surroundings of the object region of interest, into which the image data record is superimposed.

In principle, the medical-optical observation apparatus can be any medical apparatus that generates an object image, such as, for example, an operating microscope, endoscope, endomicroscope, etc.

Accordingly, the medical-optical display system can be any system that is suitable for displaying an object image that was recorded by the medical-optical observation apparatus. Examples include monitors and head-mounted displays, which receive the object image from a medical-optical observation appliance, or portions of operating microscopes, endoscopes or endomicroscopes that comprise at least one eyepiece.

The at least one image data record contains status information items about an appliance or patient data, for example, and it is present in electronic form. By way of example, it can be converted into optical data by means of a display or any other suitable converter unit, said optical data then being superimposed on, for example mirrored into, a beam path of the medical-optical display system in order to be superimposed on the beam path of the object image. However, it can also be digitally superposed on a digital object image in digital form. The at least one region with little activity can be determined with the aid of algorithms, or use is made of adaptive systems, for example on the basis of neural networks, in particular multi-layer neural networks.

According to one embodiment, the following steps are carried out for the purposes of determining the region with little activity:
  capturing raw image data records, which represent a time sequence of individual object images,
  ascertaining the time variability of image points in the raw image data records, wherein the image points can be pixels or pixel groups composed of pixels of the raw image data records, comparing the time variability to a set variability limit, and clustering those image points whose ascertained time variability lies below the variability limit in order to produce at least one contiguous area with little time variability, and specifying the at least one contiguous area with little time variability as the at least one region with little activity.

Thus, a time sequence of individual object images is captured, for example in the form of a video sequence from a video stream that was recorded of the object. Here, the raw image data records are available in electronic form. Then, at least one region with little activity, i.e. little variability of the pixels, which is suitable for superimposing the image data record, is ascertained on the basis of a comparison of the time variability of the image points in temporally successive object images to a predetermined variability limit. Then, the image data record is superimposed in one of these regions. If a plurality of image data records are present, these may be superimposed in different portions of the same region with little activity or in different regions with little activity if at least two regions with little activity are present.

In order to obtain a sufficiently large contiguous area with little time variability and suitable size for superimposing the image data record, it may be advantageous for individual contiguous areas with little time variability to be merged into a larger contiguous area with little time variability by image processing, wherein the larger contiguous area with little time variability is then specified as the at least one region with little activity.

The location in the at least one region with little activity at which the image data record is superimposed can be determined taking into account the size and/or form of the image content displayed in the image data record. As a result of this, it is possible to specify, for example, whether the at least one region with little activity suffices for superimposing the image data record or whether, where necessary, individual regions with little activity and little time variability have to be merged to a larger at least one region with little activity.

In a development of the method according to the invention, a depth map of the observation object can be used to exclude certain regions in the raw image data records, in which much activity is to be expected, in advance from being the at least one region with little activity. Additionally, or alternatively, regions in the raw image data records, in which appliance displays or faces are imaged, can be recognized on the basis of a pattern recognition and excluded in advance from being the at least one region with little activity.

A medical-optical display system according to the invention for displaying an object image obtained by a medical-optical observation apparatus comprises
 a data superimposition unit that is embodied to superimpose at least one image data record into the object image, and
 a region determination unit that is embodied to determine at least one region with little activity within the object image.

The data superimposition unit is embodied to superimpose the at least one image data record into the at least one region of the object image with little activity.

The medical-optical observation apparatus according to the invention is adapted to carrying out the method according to the invention.

Moreover, the medical-optical display system can comprise a medical-optical observation apparatus for observing an object and for recording an image of the observed object as the object image.

The region determination unit of the medical-optical display system may, in particular, comprise:
 a read-in unit for reading raw image data records, which represent a time sequence of individual object images,
 an evaluation unit for ascertaining the time variability of image points in the raw image data records, wherein the image points can be the pixels or pixel groups composed of pixels of the raw image data records,
 a comparison unit for comparing the time variability to a set variability limit,
 a cluster unit for clustering those image points whose ascertained time variability lies below the variability limit in order to produce at least one contiguous area with little time variability, and
 a specification unit for specifying the at least one contiguous area with little time variability as the at least one region with little activity.

In order to obtain a contiguous area with little time variability and suitable size for the superimposition of the image data record, an image processing unit may be present, said image processing unit merging individual contiguous areas with low time variability into a larger contiguous area with low time variability by means of morphological image processing. Then, the specification unit is configured to specify the larger contiguous area with little time variability as the at least one region with little activity.

In the medical-optical display system according to the invention, the device for the data superimposition of an image data record can be embodied to take into account the size and/or form of the image content displayed in the image data record for the purposes of determining the location in the at least one region with little activity at which the image data record is superimposed. As a result of this, it is possible to specify, for example, whether the at least one region with little activity suffices for superimposing the image content of the image data record or whether, where necessary, individual regions with little activity have to be merged to a larger contiguous region with little activity.

Optionally, in the medical-optical display system according to the invention, the region determination unit can comprise a pre-selection device which, on the basis of a depth map of the observation object excludes certain regions in the raw image data records, in which much activity is to be expected, in advance from being the at least one region with little activity and/or which, on the basis of a pattern recognition, recognizes regions in the raw image data records, in which appliance displays or faces are imaged, and excludes these in advance from being the at least one region with little activity.

Further, the invention includes a computer program product containing program code with computer-readable instructions for carrying out the method according to the invention when the program code is loaded onto a computer and/or executed on a computer.

Further features, properties and advantages of the present invention will become apparent from the following description of exemplary embodiments with reference to the accompanying figures.

DETAILED DESCRIPTION OF THE INVENTION

Figure 1:
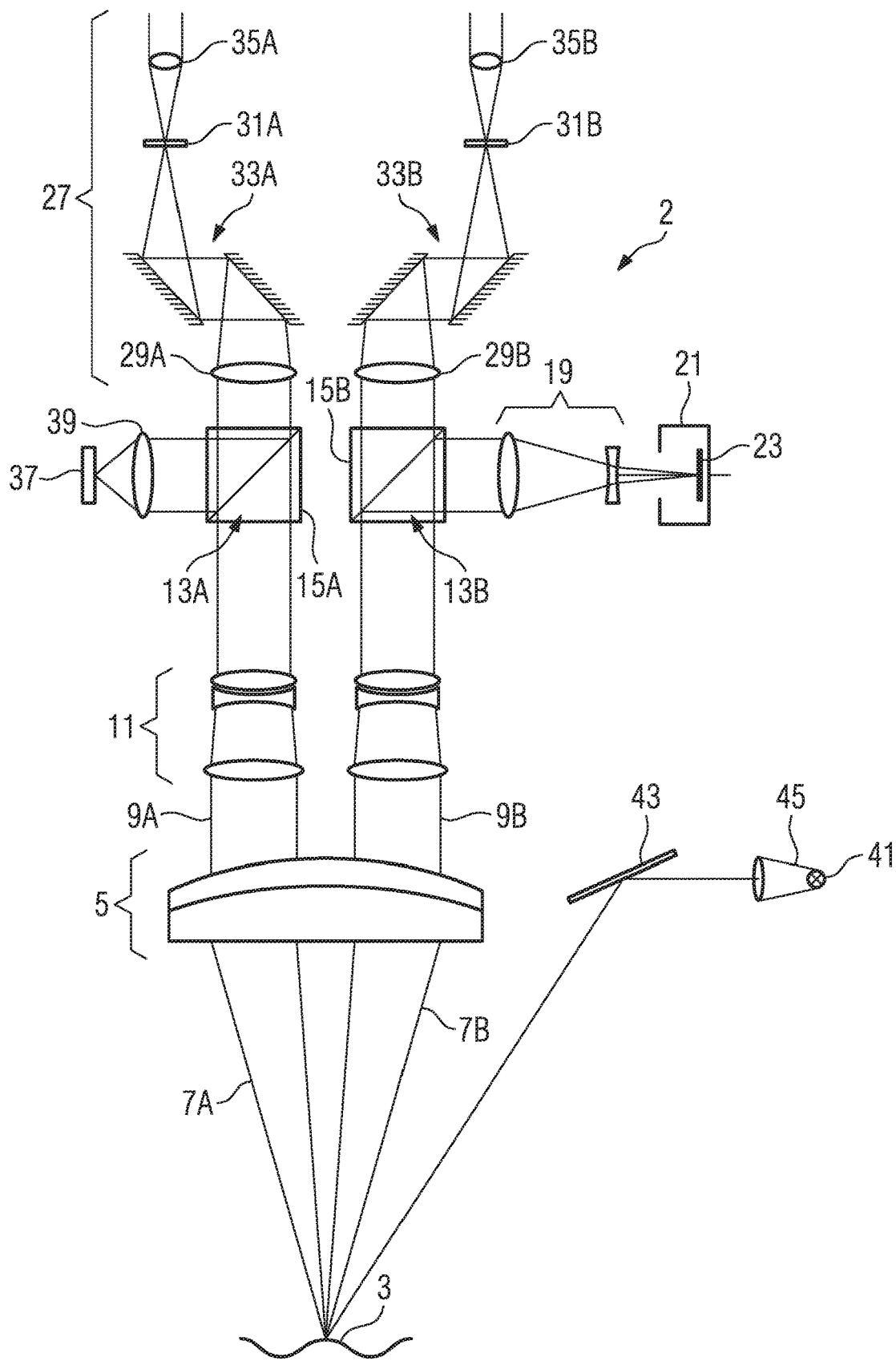
FIG. 1 shows the typical structure of an operating microscope in a schematic illustration.

Reference is made to FIG. 1, which schematically illustrates the structure of an operating microscope. In the present exemplary embodiment, the medical-optical display system is a part of the operating microscope 2.

An operating microscope 2 is understood to be a microscope that is used in minimally invasive surgery and microsurgery. It has a comparatively low magnification (approximately 6× to 40×) and, as a rule, provides a three-dimensional image. The magnification goes beyond that of magnifying spectacles. In the medical field, it is used in almost all lines of surgery.

The operating microscope 2 shown in FIG. 1 comprises an objective 5 that should face an object field 3, said objective, in particular, being able to be embodied as an achromatic or apochromatic objective. In the present exemplary embodiment, the objective 5 consists of two partial lenses that are cemented to one another and form an achromatic objective. The object field 3 is arranged in the focal plane of the objective 5 such that it is imaged at infinity by the objective 5. Expressed differently, a divergent beam 7A, 7B emanating from the object field 3 is converted into a parallel beam 9 during its passage through the objective 5.

A magnification changer 11 is arranged on the observer side of the objective 5, which magnification changer can be embodied either as a zoom system for changing the magnification factor in a continuously variable manner as in the illustrated exemplary embodiment, or as a so-called Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can be arranged in a fixed manner. In a Galilean changer, by contrast, there are a plurality of fixed lens combinations which represent different magnification factors and which can be introduced into the beam path alternately. Both a zoom system and a Galilean changer convert an object-side parallel beam into an observer-side parallel beam having a different beam diameter. In the present exemplary embodiment, the magnification changer 11 already is part of the binocular beam path of the operating microscope 2, i.e. it has a dedicated lens combination for each stereoscopic partial beam path 9A, 9B of the operating microscope 2. In the present exemplary embodiment, a magnification factor is adjusted by means of the magnification changer 11 by way of a motor-driven actuator which, together with the magnification changer 11, is part of a magnification changing unit for adjusting the magnification factor.

In the present example, the magnification changer 11 is adjoined on the observer side by an interface arrangement 13A, 13B, by means of which external appliances can be connected to the operating microscope 2 and which comprise beam splitter prisms 15A, 15B in the present exemplary embodiment. However, in principle, use can also be made of other types of beam splitters, for example partly transmissive mirrors. In the present exemplary embodiment, the interface arrangements 13A, 13B serve to output couple a beam from the beam path of the operating microscope 2 (beam splitter prism 15B) and to input couple a beam into the beam path of the operating microscope 2 (beam splitter prism 15A).

In the present exemplary embodiment, the beam splitter prism 15A in the partial beam path 9A serves to mirror information or data for a surgeon into the partial beam path 9A of the operating microscope 2 with the aid of a display 37, for example a digital mirror device (DMD) or an LCD display, and an associated optical unit 39 by means of the beam splitter prism 15A. A camera adapter 19 with a camera 21 fastened thereto, said camera being equipped with an electronic image sensor 23, for example with a CCD sensor or a CMOS sensor, is arranged at the interface arrangement 13B in the other partial beam path 9B. By means of the camera 21, it is possible to record an electronic image and, in particular, a digital image of the tissue region 3. In particular, a hyperspectral sensor also can find use as an image sensor, said hyperspectral sensor having not only three spectral channels (e.g. red, green and blue) but also a multiplicity of spectral channels. In order to be able to provide images with depth information, provision can be made for a camera with components assigned to the respective camera to be respectively provided (not illustrated here) in each partial beam path 9A, 9B. Further, provision can be made for a display with components assigned to the respective display to be respectively provided (not illustrated here) in each partial beam path 9A, 9B in order to be able to provide image data records BD with depth information.

In the present example, a binocular tube 27 adjoins the interface arrangement 13A, 13B on the observer side. It has two tube objectives 29A, 29B, which focus the respective parallel beam 9A, 9B onto a respective intermediate image plane 31A, 31B, i.e. image the observation object 3 onto the respective intermediate image plane 31A, 31B. The intermediate images situated in the intermediate image planes 31A, 31B are finally imaged at infinity in turn by eyepiece lenses 35A, 35B, such that an observer can observe the intermediate image with a relaxed eye. Moreover, an increase in the distance between the two partial beams 9A, 9B is effectuated in the binocular tube by means of a mirror system or by means of prisms 33A, 33B in order to adapt said distance to the intraocular distance of the observer. In addition, image erection is carried out by the mirror system or the prisms 33A, 33B.

In this operating microscope, the binocular tube 27 and the interface arrangement 13A, 13B form the medical-optical display system, with the data superimposition unit being formed by the beam splitter prism 15A and the display 37 and the optical unit 39.

The operating microscope 2 moreover is equipped with an illumination apparatus, by means of which the object field 3 can be illuminated with broadband illumination light. To this end, the illumination apparatus has a white-light source 41, for example a halogen lamp or a gas discharge lamp, in the present example. The light emanating from the white-light source 41 is directed in the direction of the object field 3 via a deflection mirror 43 or a deflection prism in order to illuminate said field. Furthermore, an illumination optical unit 45 is present in the illumination apparatus, said illumination optical unit ensuring uniform illumination of the entire observed object field 3.

Reference is made to the fact that the illumination beam path illustrated in FIG. 1 is very schematic and does not necessarily reproduce the actual course of the illumination beam path. In principle, the illumination beam path can be embodied as a so-called oblique illumination, which comes closest to the schematic illustration in FIG. 1. In such oblique illumination, the beam path extends at a relatively large angle (6° or more) with respect to the optical axis of the objective 5 and, as illustrated in FIG. 1, may extend completely outside the objective. Alternatively, however, there is also the possibility of allowing the illumination beam path of the oblique illumination to extend through a marginal region of the objective 5. A further option for the arrangement of the illumination beam path is the so-called 0° illumination, in which the illumination beam path extends through the objective 5 and is input coupled into the objective between the two partial beam paths 9A, 9B, along the optical axis of the objective 5 in the direction of the object field 3. Finally, it is also possible to embody the illumination beam path as a so-called coaxial illumination, in which a first illumination partial beam path and a second illumination partial beam path are present. The illumination partial beam paths are input coupled into the operating microscope 2 in a manner parallel to the optical axes of the observation partial beam paths 9A, 9B by way of one or more beam splitters such that the illumination extends coaxially in relation to the two observation partial beam paths.

In the embodiment variant of the operating microscope 2 shown in FIG. 1, the objective 5 only consists of an achromatic lens with a fixed focal length. However, use can also be made of an objective lens system made of a plurality of lenses, in particular a so-called varioscope objective, by means of which it is possible to vary the working distance of the operating microscope 2, i.e. the distance between the object-side focal plane and the vertex of the first object-side lens surface of the objective 5, also referred to as front focal distance. The object field 3 arranged in the focal plane is imaged at infinity by the varioscope objective 50, too, and so a parallel beam is present on the observer side.

Figure 2:
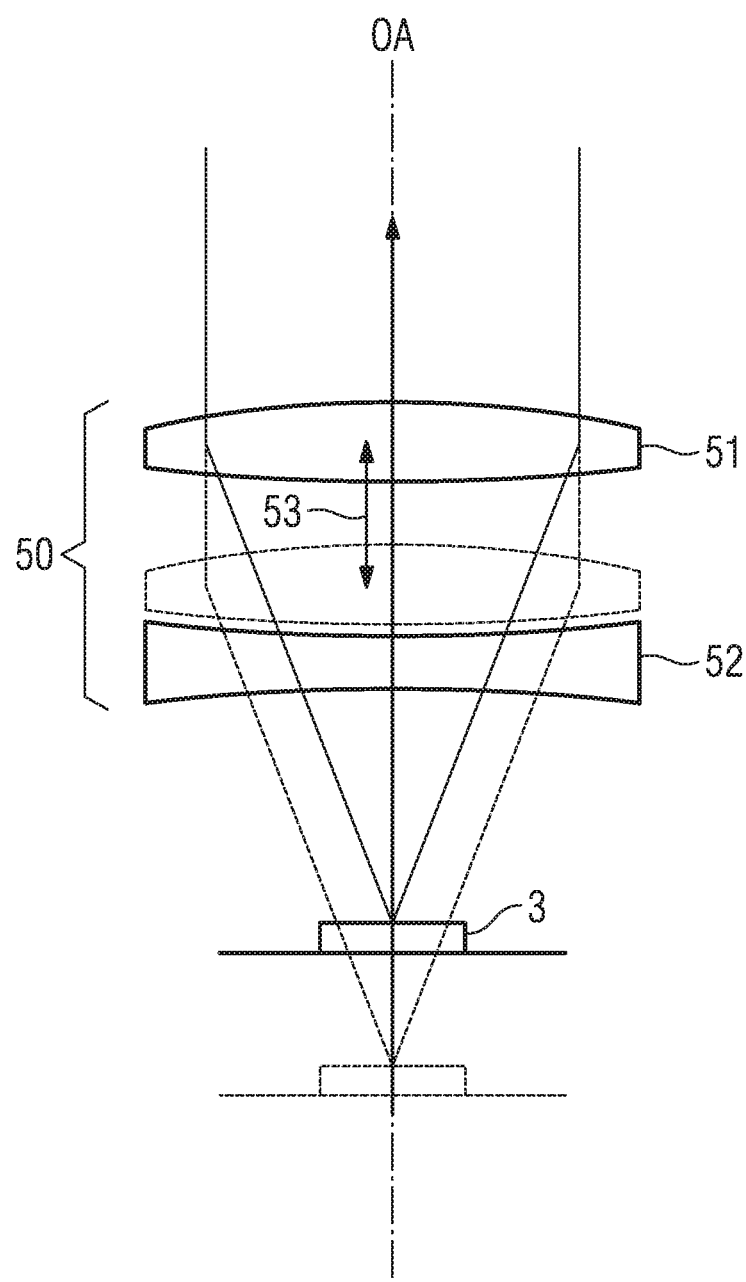
FIG. 2 shows an objective for an operating microscope which can be used instead of the objective illustrated in FIG. 1.

One example of a varioscope objective is illustrated schematically in FIG. 2. The varioscope objective 50 comprises a positive member 51, i.e. an optical element having positive refractive power, which is schematically illustrated as a convex lens in FIG. 2. Moreover, the varioscope objective 50 comprises a negative member 52, i.e. an optical element having negative refractive power, which is schematically illustrated as a concave lens in FIG. 2. The negative member 52 is situated between the positive member 51 and the object field 3. In the illustrated varioscope objective 50, the negative member 52 has a fixed or immovable arrangement, whereas, as indicated by the double-headed arrow 53, the positive member 51 is arranged to be displaceable along the optical axis OA. When the positive member 51 is displaced into the position illustrated by dashed lines in FIG. 2, the back focal length increases, and so there is a change in the working distance of the operating microscope 2 from the object field 3.

Even though the positive member 51 has a displaceable configuration in FIG. 2, it is also possible, in principle, to arrange the negative member 52 to be movable along the optical axis OA instead of the positive member 51. However, the negative member 52 often forms the last lens of the varioscope objective 50. A stationary negative member 52 therefore offers the advantage of making it easier to seal the interior of the operating microscope 2 from external influences. Furthermore, it is noted that, even though the positive member 51 and the negative member 52 in FIG. 2 are only illustrated as individual lenses, each of these members may also be realized in the form of a lens group or a cemented element instead of in the form of an individual lens, e.g. in order to embody the varioscope objective to be achromatic or apochromatic.

Figure 3:
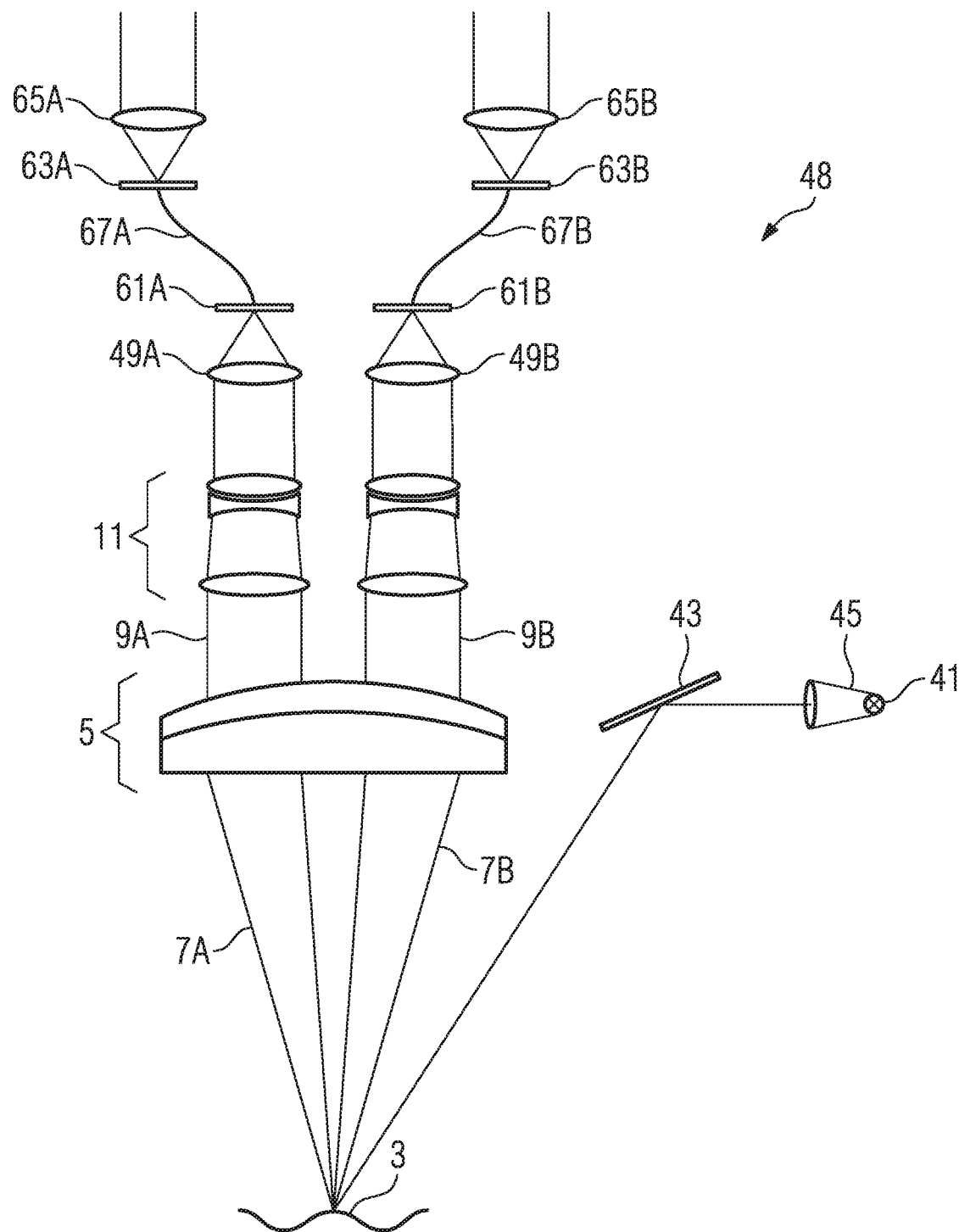
FIG. 3 shows an alternative configuration of the operating microscope.

FIG. 3 shows a schematic illustration of an example of a digital operating microscope 48. In this operating microscope 48, the main objective 5, the magnification changer 11 and the illumination system 41, 43, 45 do not differ from the operating microscope 2 with the optical eyepiece that is illustrated in FIG. 1. The difference lies in the fact that the operating microscope 48 shown in FIG. 3 does not comprise an optical binocular tube. Instead of the tube objectives 29A, 29B from FIG. 1, the operating microscope 48 from FIG. 3 comprises focusing lenses 49A, 49B, by means of which the binocular observation beam paths 9A, 9B are imaged onto digital image sensors 61A, 61B. Here, the digital image sensors 61A, 61B can be e.g. CCD sensors or CMOS sensors. The images recorded by the image sensors 61A, 61B are transmitted digitally to digital displays 63A, 63B, which may be embodied as LED displays, as LCD displays or as displays based on organic light-emitting diodes (OLEDs). Like in the present example, eyepiece lenses 65A, 65B can be assigned to the displays 63A, 63B, by means of which the images displayed on the displays 63A, 63B are imaged at infinity such that an observer can observe said images with relaxed eyes. In this operating microscope, the displays 63A, 63B and the eyepiece lenses 65A, 65B form the medical-optical display system. Here, the data superimposition unit is a digital unit for superimposing an image data record into at least one of the images displayed on the displays 63A, 63B. The image of the image data record is electronically superposed on the corresponding image. The displays 63A, 63B and the eyepiece lenses 65A, 65B can be part of a digital binocular tube; however, they can also be part of a head-mounted display (HMD) such as e.g. a pair of smartglasses. The head-mounted display can be embodied as a virtual reality display or as an augmented reality display.

Even though FIG. 3, like FIG. 1, only illustrates an achromatic lens 5 with a fixed focal length, the operating microscope 48 shown in FIG. 3 may comprise a varioscope objective instead of the objective lens 5, like the operating microscope 2 illustrated in FIG. 1. Furthermore, FIG. 3 shows a transfer of the images recorded by the image sensors 61A, 61B to the displays 63A, 63B by means of lines 67A, 67B. However, instead of in a wired manner, the images can also be transferred wirelessly to the displays 63A, 63B, especially if the displays 63A, 63B are part of a head-mounted display.

Figure 4:
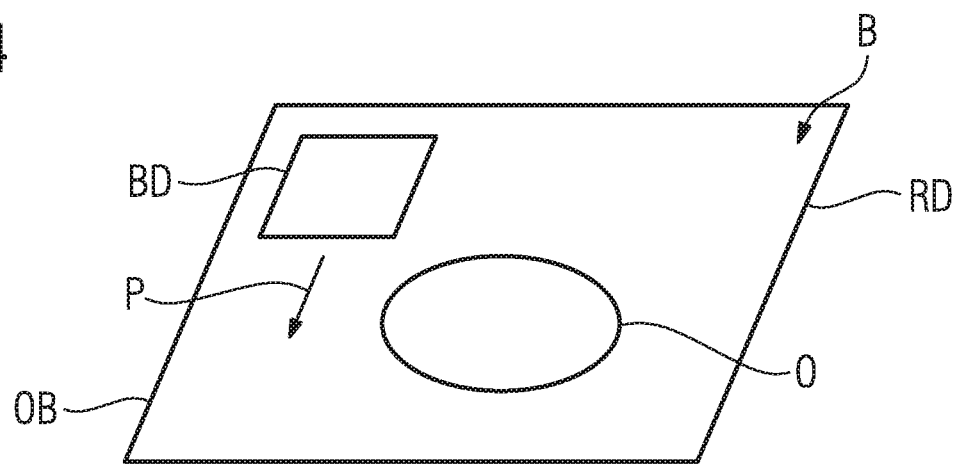
FIG. 4 shows a scenario in which a medical-optical display system is used.

Reference is now additionally made to FIG. 4.

A scenario in which a surgeon observes an object image OB, obtained from the object O by means of the operating microscope 2, with the aid of the medical-optical display system is illustrated. The object O can be an individual object or a group of objects. Further, the object O can also be a region, such as an operating field, for example, and so this can also be a region of interest (ROI). Then, the remaining regions of the object image OB show the surroundings of the operating field. It should be noted that the object image OB passes through the beam path of the operating microscope 2 illustrated in FIG. 1 or of the operating microscope 48 illustrated in FIG. 3. Expressed differently, the object images are optical data which are illustrated optically or electronically.

In order to provide additional information items, such as status reports of an appliance, to the surgeon, the medical-optical display system has an apparatus for superimposing data of an image data record BD into the object image OB, with the visualization of the image data record BD providing the additional information items. To this end, the device comprises e.g. the interface arrangement 13B with the beam splitter prism 15B and the display 37 with the assigned optical unit 39. Thus, during operation, the image data record BD that is present in electronic form is converted into optical data by the display 37 and input coupled or mirrored into the beam path of the operating microscope 2. Deviating therefrom, the superimposition may also comprise an electronic superposition of image contents, i.e. the image data record BD is present in electronic form and inserted into images that are present electronically (as is the case, for example, in the operating microscope 48 shown in FIG. 3) by virtue of replacing a portion of the image or overlaying said portion in an electronically transparent or opaque fashion.

Figure 5:
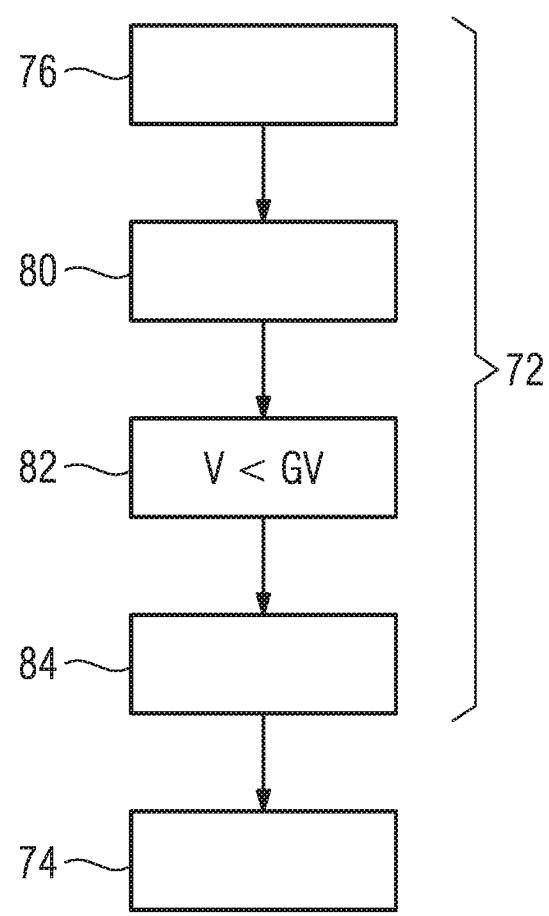
FIG. 5 shows an exemplary embodiment of an apparatus for carrying out a method according to the invention.

Now, with additional reference to FIG. 5, explanations are provided in relation to the structure of an apparatus 70 that, during operation, ensures that relevant image content of the object image OB is not masked during the data superimposition of the image data record BD.

In the present exemplary embodiment, the apparatus 70 has a region determination unit 72 and a data superimposition unit 74. Using the region determination unit 72, it is possible to determine a region B with little activity within the object images OB, while the data superimposition unit 74 can be used to superimpose the image data record BD in this region B. Here, a region B with little activity can be, for example, a region in the object image OB in which the surgeon is not active and in which there are therefore only minor changes to image contents. Changes that are not minor or a high variability of the image contents are present if, for example, a surgeon is active with its fingers in the corresponding area or if a surgical instrument is on the move. As a result, there is a strong change in the intensity values of the respective pixels.

In the present exemplary embodiment, the region determination unit 72 has a read-in unit 76, an evaluation unit 80, a comparison unit 82, a cluster unit 84 and a specification unit 86.

The read-in unit 76 reads the raw image data records RD. The raw image data records RD form a time sequence of individual object images OB, which reproduce the temporal profile of the happenings shown in the object images OB. Here, the raw image data records RD can be a video sequence of a video stream recorded of the object O. Here, the raw image data records can be generated, for example, by means of the camera 21 from FIG. 1 or by means of the image sensors 61A, 61B from FIG. 3. If use is made of a plurality of cameras 21, the respective raw image data records are initially fusioned (registered or stitched). Preferably, the raw image data records RD do not contain the superimposed image data record BD, at least if the superimposed image data record BD contains time-varying image contents.

The evaluation unit 80 ascertains the time variability V of image points of the raw image data records. It is representative for temporal changes in the image portion represented by the image points. Here, the image points can be either the pixels of the raw image data records RD or pixel groups made of 2×2, 2×3, 2×4, 3×3, 3×4, 4×4, etc., pixels of the raw image data records RD. By way of example, the time variability can be ascertained here by summing the absolute values of pixel value differences between the same pixels in temporally successive raw images. The more frequently pixel value differences with large absolute values occur, the larger the sum becomes. By contrast, the sum remains small in the case of pixel value differences with only small absolute values. In the case of pixel groups, the sum of contributions of differences of pixel values averaged over the pixel groups can be summed accordingly. When forming the sums, use is preferably made of object images which, proceeding from the current object image, go back a certain duration in time. This time duration may be adjustable in order to be able to adapt it to different temporal dynamics of image contents. Quickly changing image contents require a shorter time duration in this case than slowly changing image contents.

The comparison unit 82 compares the time variability V to a set variability limit GV. The latter may be adjustable in order to be able to take into account the expected time variability V of the image points in the regions B with little activity. If relatively little time variability V is expected in the regions B, the variability limit can be kept lower than if relatively high time variability V is to be expected in the regions B (which time variability, however, still is lower than in the regions with much activity).

The cluster unit 84 clusters those image points whose ascertained time variability lies below the variability limit GV. As a result of clustering, one or more contiguous areas with little time variability are formed. Optionally, an image processing unit moreover may be present, said image processing unit merging individual ones of the contiguous areas with low time variability into a larger contiguous area with low time variability by morphological image processing. Then, the specification unit 86 specifies the at least one contiguous area with little time variability as the region B with little activity.

In the present exemplary embodiment, the data superimposition unit 74 is embodied to take account of size and/or form of the image data record BD for the purposes of determining the location in the region B with little activity at which the image data record is superimposed in order to undertake the superimposition at a site in the region B with little activity that is suited to the size and form of the image data record BD to be superimposed.

Figure 6:
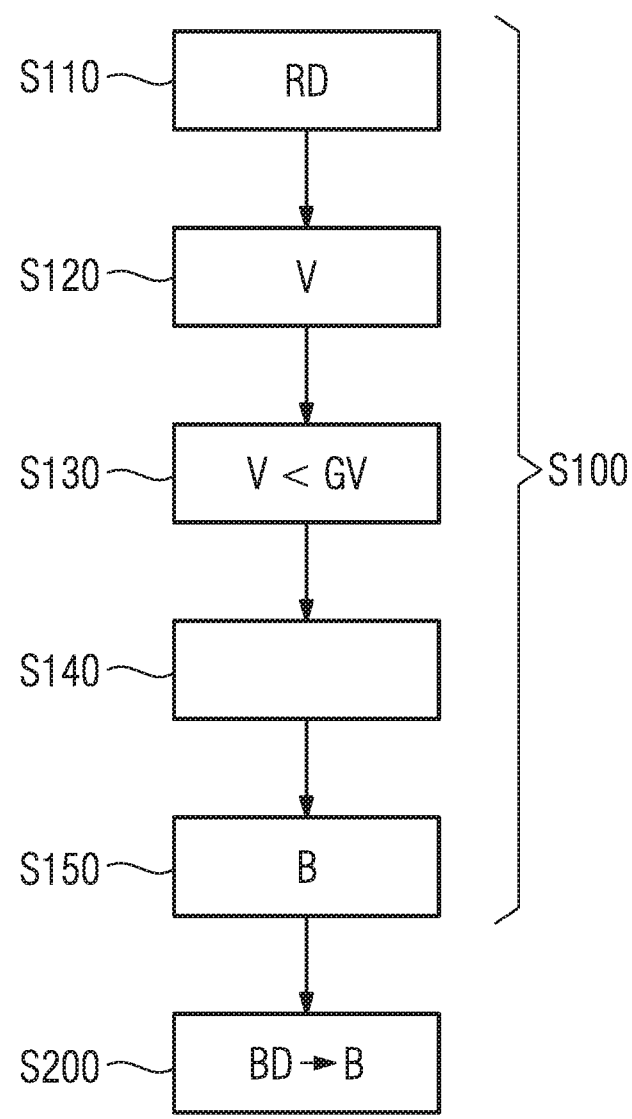
FIG. 6 shows a flowchart of an exemplary embodiment of a method according to the invention.

Now, with additional reference to FIG. 6, a method is explained which ensures that image contents of the object image OB are not masked during the data superimposition of the image data record BD. To this end, a region B with little activity is ascertained within the object image OB in a first step S100. Then, the image data record BD is superimposed into the ascertained region B in a further step S200.

In order to ascertain the region B with little activity, raw image data records RD of the object image OB are captured in the intermediate step S110 and the time variability V of image points of the raw image data records is ascertained (intermediate step S120). The ascertained time variability V is compared to a set variability limit GV (intermediate step S130) and those pixels whose ascertained time variability lies below the variability limit GV are clustered (intermediate step S140) in order to produce at least one contiguous area with little time variability. Finally, the at least one contiguous area with little time variability is specified as region B with little activity (intermediate step S150).

In a development of the method, a depth map of the observation object can serve to exclude certain regions, in which much activity is to be expected, in advance. By way of example, in the case of deep operating channels, much activity is to be expected, particularly in the region of the operating channels.

The steps with which a region B with little activity is ascertained within the object image OB can be carried out using a suitable algorithm. By way of example, a possible algorithmic approach is that of an analysis by means of an optical flow or by means of machine learning, for instance with neural networks. The method can be carried out on a PC or computer which has a data-transmitting link to the medical-optical observation apparatus in order to read the data from the camera 21 and to output the image data record BD for actuating the display 37. To this end, the PC or computer can have appropriate hardware and/or software components. Alternatively, the method can also be carried out by a computer assembly with appropriate hardware and/or software components, said computer assembly belonging to the medical-optical observation apparatus.

The present invention has been described in detail on the basis of exemplary embodiments for explanation purposes. However, a person skilled in the art recognizes that there may be deviations from the exemplary embodiments within the scope of the present invention. By way of example, deviating from the present exemplary embodiments, the medical-optical display system may be embodied as part of an endoscope or endomicroscope. A person skilled in the art will identify further options for developing the exemplary embodiments within the scope of the invention. Therefore, the present invention is not intended to be restricted to the described exemplary embodiments, but rather only by the appended claims.

LIST OF REFERENCE SIGNS

2 Operating microscope
3 Operating field/observation object
5 Objective
7 Beam
9 Beam
9A Stereoscopic partial beam path
9B Stereoscopic partial beam path
11 Magnification changer
13A Interface arrangement
13B Interface arrangement
15A Beam splitter prism
15B Beam splitter prism
19 Camera adapter
21 Camera
23 Image sensor
27 Binocular tube
29A Tube objective
29B Tube objective
31A Intermediate image plane
31B Intermediate image plane
33A Prism
33B Prism
35A Eyepiece lens
35B Eyepiece lens
37 Display
39 Optical unit
41 White light source
43 Deflection mirror
45 Illumination optical unit
48 Operating microscope
49A Focusing lens
49B Focusing lens
50 Varifocal objective
51 Positive member
52 Negative member
53 Double-headed arrow
61A Image sensor
61B Image sensor
63A Display
63B Display
65A Eyepiece lens
65B Eyepiece lens
67A Line
67B Line
70 Apparatus
72 Region determination unit
74 Data superimposition unit
76 Read-in unit
80 Evaluation unit
82 Comparison unit
84 Cluster unit
86 Specification unit
B Region
BD Image data record
O Object
OA Optical axis
OB Object image
RD Raw image data record
V Variability
GV Variability limit
S100 Determining a region with little activity
S110 Capturing raw image data records
S120 Ascertaining the time variability of image points
S130 Comparing the time variability to a set variability limit
S140 Clustering
S150 Specifying the region with little activity
S200 Superimposing the image data record

The invention claimed is:

1. A method for operating a medical-optical display system for displaying an object image (OB) of an observed object (O), said object image having been obtained by means of a medical-optical observation apparatus wherein the medical-optical display system comprises a data superimposition unit for superimposing data of at least one image data record (BD) into the object image (OB), said method including the steps of:
    determining at least one region (B) with little activity within the object image (OB) by:
    capturing raw image data records (RD), which represent a time sequence of individual object images (OB),
    ascertaining the time variability of image points in the raw image data records (RD),
    comparing the time variability (V) to a set variability limit (GV);
    clustering those image points whose ascertained time variability lies below the variability limit (GV) in order to produce at least one contiguous area with little time variability; and
    specifying the at least one contiguous area with little time variability as the at least one region (B) with little activity; and
    superimposing the at least one image data record (BD) into the at least one region (B) with little activity.

2. The method according to claim 1, wherein individual contiguous areas with little time variability are merged into a larger contiguous area with little time variability by image processing and wherein the larger contiguous area with little time variability is specified as the at least one region (B) with little activity.

3. The method according to claim 1, wherein the image points are the pixels of the raw image data records (RD).

4. The method according to claim 1, wherein the image points are pixel groups, composed of pixels, of the raw image data records (RD).

5. The method according to claim 1, wherein the location in the at least one region (B) with little activity at which the image data record (BD) is superimposed is determined taking into account the size and/or form of the image content displayed in the image data record (BD).

6. The method according to claim 1, wherein a depth map of the observation object (O) is used to exclude certain regions in the raw image data records (RD), in which much activity is to be expected, in advance from being the at least one region (B) with little activity and/or wherein regions in the raw image data records (RD), in which appliance displays or faces are imaged, are recognized on the basis of a pattern recognition and excluded in advance from being the at least one region (B) with little activity.

7. A non-transitory computer-readable medium storing computer-readable code for carrying out the method according to claim 1 when the computer-program code is executed on a computer.

8. A medical-optical display system for displaying an object image (OB) obtained by a medical-optical observation apparatus having
   a data superimposition unit that is embodied to superimpose at least one image data record (BD) into the object image (OB), and
   a region determination unit that is embodied to determine at least one region (B) with little activity within the object image (OB), the region determination unit comprising:
     a read-in unit for reading raw image data records (RD), which represent a time sequence of individual object images (OB),
     an evaluation unit for ascertaining the time variability of image points in the raw image data records (RD),
     a comparison unit for comparing the time variability (V) to a set variability limit (GV),
     a cluster unit for clustering those image points whose ascertained time variability lies below the variability limit (GV) in order to produce at least one contiguous area with little time variability, and
     a specification unit for specifying the at least one contiguous area with little time variability as the at least one region (B) with little activity,
   wherein the data superimposition unit is embodied to superimpose the at least one image data record (BD) into the at least one region (B) of the object image (OB) with little activity.

9. The medical-optical display system according to claim 8, moreover comprising a medical-optical observation apparatus for observing an object (O) and for recording an image of the observed object (O) as the object image (OB).

10. The medical-optical display system according to claim 8, wherein
   an image processing unit is present, said image processing unit merging individual contiguous areas with low time variability into a larger contiguous area with low time variability by image processing, and
   the specification unit is configured to specify the larger contiguous area with little time variability as the at least one region (B) with little activity.

11. The medical-optical display system according to claim 8, wherein the image points are the pixels of the raw image data records (RD).

12. The medical-optical display system according to claim 8, wherein the image points are pixel groups, composed of pixels, of the raw image data records (RD).

13. The medical-optical display system according to claim 8, wherein the data superimposition unit is embodied to take into account the size and/or form of the image content displayed in the image data record (BD) for the purposes of determining the location in the at least one region (B) with little activity at which the at least one image data record (BD) is superimposed.

14. The medical-optical display system according to claim 8, wherein the region determination unit comprises a pre-selection device which, on the basis of a depth map of the observation object (O), excludes certain regions in the raw image data records (RD), in which much activity is to be expected, in advance from being the at least one region (B) with little activity and/or which, on the basis of a pattern recognition, excludes regions in the raw image data records (RD), in which appliance displays or faces are imaged, in advance from being the at least one region (B) with little activity.

* * * * *